(12) United States Patent
Carlson et al.

(10) Patent No.: US 8,061,079 B2
(45) Date of Patent: Nov. 22, 2011

(54) METHOD FOR SELECTING CONIFER TREES

(75) Inventors: William C. Carlson, Olympia, WA (US); Christine A. Dean, Puyallup, WA (US); James A. Grob, Bonnie Lake, WA (US); George E. Herold, Rochester, WA (US); Erin Wallich, Kaleden (CA)

(73) Assignee: Weyerhaeuser NR Company, Federal Way, WA (US)

( * ) Notice: Subject to any disclaimer, the term of this patent is extended or adjusted under 35 U.S.C. 154(b) by 17 days.

(21) Appl. No.: 11/171,157

(22) Filed: Jun. 29, 2005

(65) Prior Publication Data

US 2007/0017152 A1 Jan. 25, 2007

(51) Int. Cl.
*A01H 3/00* (2006.01)
(52) U.S. Cl. .................................... 47/58.1 R; 800/319
(58) Field of Classification Search ............... 47/58.1 R; 800/319
See application file for complete search history.

(56) References Cited

PUBLICATIONS

Barnes et al. Genetic control of fifth year traits in *Pinus patula* Schiede and Deppe. Silvae Genetica 41, 4-5, 1992, pp. 242-248.*
Carter et al. Symptoms and Causes of Distorted Growth in Immature Forest Stands in Coastal British Columbia. Land Management Report No. 39, 1986, pp. 23-36.*
Cline et al. Hormonal control of second flushing in Douglas-fir shoots. Tree Physiology 26, 1369-1375, 2006.*
Cline. Execution of the auxin replacement apical dominance experiment in termperate woody species. American Journal of Botany 87(2): 182-1900, 2000.*
Harmer. Differences in growth and branch production by young plants of two provenances of *Quercus robur* L. Forestyr, vol. 73, No. 3, 2000, pp. 271-281.*
McKeand et al. Growth and stem sinuosity of diverse provenances of three-year-old Loblolly pine. In: Proc. 22nd Southern Forest Tree Improvement Conference, 1993, 208-213.*
Notes on Elm in the Korqin Sandy Lands, 2002. Northeast China. Retrieved from the Internet on Apr. 27, 2007 at <http://www.fao.org/DOCREP/006/AD110E/AD110E02.htm> 15 pages.*
Powell. Shoot elongation, leaf demography and bud formation in relation to branch position on *Larix laricina* saplings. Trees, 1998, 2: 150-164.*
Schermann et al. Genetic parameters of stem form traits in a 9-year-old coastal Douglas-fir progeny test in Washington. Silvae Genetica, 1997, 46, 2-3, pp. 166-170.*
Will. Nitrogen supply, apical dominance and branch growth in *Pinus radiata*. Plant and Soil 34, 515-517 (1971).*
Adams et al. Genetics of Second Flushing in a French Plantation of Coastal Douglas-Fir, Silvae Genetica 43, 5/6 (1994), pp. 345-352.*
Bail et al. Stem deformity in *Pinus radiata* on highly fertile sites:expression and genetic variation. Aust. For. 1989, 52 (4), pp. 309-320.*
Partanen et al. Effect of Accumulated Duration of the Light Period on Bud Burst in Norway Spruce (*Picea abies*) of Varying ages. Silva Fennica 35(1) 2001, pp. 111-117.*
Kaya et al. The pattern of genetic variation in shoot growth of *Pinus bruita* Ten. populations sampled from the Toros Mountains in Turkey. Silvae Genetica, 46, 2-3, 1997, pp. 73-81.*
King et al. Selection of growth and yield traits in controlled crosses of coastal Douglas-fir. Silvae Genetica 37, 3-4 (1988), pp. 158-164.*
Rudolph. Lammas growth and prolepsis in Jack pine in the Lake States. Forest Science Monograph Jun. 1964, pp. 1-70.*
Hunt. Ninth-Year Performance of Slash and Loblolly Pine Nursery Selections in Georgia. Forestry Research Technician, Southeastern Forest Experiment Station, 1967, pp. 92-94.*
Cornelius. The effectiveness of plus-treee selection for yield. Fores Ecology and Management 67 (1994) 23-34.*
Howe et al. Genetics of Stem Quality in Coastal Douglas-fir. Genetic improvement of wood quality in coastal Dougla-fir and western hemlock. Oregon State University College of Forestry 2002, pp. 67-71.*
Li et al. Genetic control of bud phenology in pole-size trees and seedlings of coastal Douglas-fir. Can. J. For. Res. 23, 1993, pp. 1043-1051.*
Heiner et al. Early Growth and Drought Avoidance in Douglas-fir Seedlings. Forest Research Laboratory, Research paper 14, 1972, pp. 1-7.*
Lambeth. Juvenile-Mature Correlations in Pinaceae and Implications for Early Selection. Forest Sci., vol. 26, No. 4, 1980, pp. 571-580.*
Abdel-Gadir et al., "Genetic variation in the age of demarcation between juvenile and mature wood in Douglas-fir," *Wood and Fiber Sc* 25(4) 1993, pp. 384-394.
Adams GW et al, "Multi-trait selection in jack pine," *Can J For Res* 21 1991, pp. 439-445.
Aubry CA et al., "Determination of relative economic weights for multitrait selection in coastal Douglas-Fir, "*Can J For Res* 28 1998, pp. 1164-1170.
Bruce D et al., "Volume equations for second-growth Douglas-fir," *USDA Forest Service Res* 239 1974 pp. 1-6.
Campbell RK "Phenotypic correlation among branch and upper-crown stem attributes in Douglas-Fir," *For Sci* 9(4) 1963, pp. 444-451.
Cline MG, "Exogenous auxin effects on lateral bud outgrowth in decapitated shoots," *Ann Bot Co* 78 1996 pp. 255-266.
Cotterill PP *Successful Tree Breeding with Index Selection* CSIRO Publications 1990 pp. 28-32.
Cotterill PP et al., "Estimates of genetic parameters for growth and form traits in four *Pinus radiata* D. Don Progency Tests in South Australia," *Aust For Res* 10 1980 pp. 155-167.
Dodd R et al., "Kinetics of tracheid differentiation in Douglas-fir," *Ann Bot Co* 65 1990 pp. 649-657.
Enquist BJ et al., "Global allocation rules of patterns of biomass partitioning in seed plants," *Sic* 295 Feb. 2002 pp. 1517-1520.
Gonzalez JS et al., "Early selection for wood density in young coastal Douglas-fir trees," *Can J For Res* 18 1988 pp. 1182-1185.
Hannrup B et al., "Genetic correlations among wood, growth capacity and stem traits in *Pinus sylvestris*," *Scan J For Res* 15 2000 pp. 161-170.

(Continued)

*Primary Examiner* — June Hwu
(74) *Attorney, Agent, or Firm* — Christensen O'Connor Johnson Kindness LLC

(57) ABSTRACT

A method for selecting conifer trees is disclosed. This method relates to the early measurement of tree characteristics for selecting trees most likely to exhibit certain traits as they mature. This method can be used for implementing silvicultural treatments, thinning or further breeding.

5 Claims, No Drawings

PUBLICATIONS

Hannrup B et al., "Genetic parameters of growth and wood quality traits in *Picea abies*," *Scan J For Res* 19 2004 pp. 14-29.

Jayawickrama KJS, "Date of earlywood-latewood transition in provenances and families of loblolly pine, and its relations to growth phenology and juvenile wood specific gravity," *Can J For Res* 27 1997 pp. 1245-1253.

Jermstad KD et al., "Mapping of quantitative trait loci controlling adaptive traits in coastal Douglas-fir. II. Spring and fall cold-hardiness," *Theor Appl Genet* 102 2001 pp. 1152-1158.

Kaya Z et al., "Correlated responses of height increment and components of increment in 2-year-old Douglas-fir," *Can J For Res* 19 1989 pp. 1124-1130.

Keil B "PETE puts panels in perspective,"*Woodbased Panels Intl* 17 1997, pp. 52,55,57,58

King JN et al, "Selection of crown form traits in controlled crosses of coastal Douglas-fir," *Silvae Genetica* 41 1992 pp. 362-370.

King JN et al, "Selection of wood density and diameter in controlled crosses of coastal Douglas-fir," *Silvae Genetica* 37 1988 pp. 152-157.

Kucera B "A hypothesis relating current annual height increment to juvenile wood formation in Norway Spruce," *Wood and Fiber Sci* 26(1) 1994 pp. 152-167.

Li P et al., "Genetic control of bud phenology in pole-size trees and seedlings of coastal Douglas-fir," *Can J For Res* 23 1993 pp. 1043-1051.

Megraw RA et al, "Detailed DBH density profiles of several trees from Douglas-Fir fertilizer/thinning plots," *Proc Symp Effect of Growth Acel on Prop of Wood* 1972 pp. G1-G24.

Persson A "How genotype and silviculture interact in forming timber properties," *Silva Fennica* 28 pp. 275-282, 1994.

Rehfeldt GE "Genetic variability within Douglas-Fir populations: Implications for Tree Improvement," *Silva Genetica* 32 1983 pp. 9-14.

St. Clair JB "Genetic variation in tree structure and its relation to size in Douglas-fir I. Biomass partitioning, foliage efficiency, stem form, and wood density," *Can J For Res* 24 1994 pp. 1226-1235.

St. Clair JB "Genetic variation in tree structure and its relation to size in Douglas-fir II. Crown form, branch characteristics, and foliage characters," *Can J For Res* 24 1994. pp. 1236-1247.

Senft JF et al., "Property profile in 60-year-old Douglas-fir," *Proceedings: A Technical Workshop: Juvenile Wood—What does it mean to foirest management and forest products?* 1985 pp. 17-28.

Shinozaki K et al., "A quantitative analysis of plant form—The pipe model theory II. Further evidence of the theory and its application in forest ecology," *Jap J of Ecol* 14 1964 pp. 133-326.

Spelter H "Plywood niche narrows but producers still have ample opportunities," *PanelWorld* 38 1997 pp. 28-31.

Sack L "Global allocation rules for patterns of biomass partitioning," *Sci* 296 2002 p. 1923a.

Thimann KV et al "On the inhibition of bud development and o ther functions of growth substance in *Vicia faba*," vol. CXIV pp. 317-326, 1934.

Uggla C et al., "Function and dynamics of auxin and carbohydrates during earlywood/latewood transition in Scots Pine," *Plant Physiol* 125 2001 pp. 2029-2039.

Vargas-Hernandez J "Age-age correlations and early selection for wood density in young coastal Douglas-fir," *For Sci* 38 1992 pp. 467-478.

Vargas-Hernandez J et al., "Family variation in age trends of wood density traits in young coastal Douglas-fir," *Wood and Fiber Sci* 26 1994 pp. 229-236.

Vargas-Hernandez J et al., "Genetic relationships between wood density components and cambial growth rhythm in young coastal Douglas-fir," *Can J For Res* 24 1994 pp. 1871-1876.

Vargas-Hernandez J et al., "Genetic variation in wood density components in young coastal Douglas-fir: implications for tree breeding," *Can J For Res* 21 1991 pp. 18701-1807.

Vargas-Hernandez J et al., "Quantitative genetic structure of stem form and branching traits in Douglas-fir seedlings and implications for early selection," *Silvae Genetica* 52 2003 pp. 36-44.

Woods JH et al., "Early selection of coastal Douglas-fir in a farm-field test environment,"*Silvae Genetica* 44 1995 pp. 178-186.

\* cited by examiner

METHOD FOR SELECTING CONIFER TREES

FIELD OF THE INVENTION

The present invention relates to a method for selecting conifer trees for improved volume, yield and wood quality.

BACKGROUND OF THE INVENTION

The growth attributes and physical characteristics of a conifer tree contribute to the value assessed that tree after a commercial harvest. Such value may be measured by the stem quality, volume of wood and wood quality measures such as strength and stiffness. The earlier these characteristics can be accurately assessed, the more a given site can be planted with trees that provide larger volume and more desirable wood characteristics per acre.

DETAILED DESCRIPTION OF THE INVENTION

The present invention relates to a method for selecting conifer trees. Conifer trees grow well in many regions, including Douglas-fir in the Pacific Northwest region of the United States and loblolly pine in the Southeast region of the United States. In the Southern hemisphere, radiata pine grows well.

The method of the present invention may be used in selecting trees for breeding based upon characteristics measured in those trees using the methods of the present invention. By using more elite trees for breeding, one is able to plant trees which are more likely to provide higher volumes of wood and more desirable characteristics.

The method of the present invention may also be used for selecting against trees for silvicultural treatments. This may include thinning or removal trees not selected based upon characteristics measured using the methods of the present invention.

The method of the present invention may also be used for a combination of selecting elite trees for breeding and later use of the method for selecting among the resulting trees for silvicultural treatments.

The method of the present invention may also be used to select a group of trees having a range of a certain characteristic to provide diversity in a site.

One factor which may be measured in the present invention is sinuosity. Generally, sinuosity is measured as the amount of stem deflection from vertical plumb in the tree. Increased amounts of sinuosity in a tree causes warped grain that impacts the quality of lumber and percent of yield of lumber and pulp from that tree.

Another factor which may be measured in the present invention is ramicorn branching or cluster knots. A ramicorn branch is highly angled (usually less than 30° to the trunk or stem).

Ramicorn branching may result from second flushing or damage to the terminal bud. Cluster knots or double whorls may result from second flushes during the same growing season. Both ramicorn branching and cluster knots can reduce the yield and quality of lumber from a tree.

EXAMPLE

Douglas-fir trees were planted on three Weyerhaeuser sites, one near Longview, Wash. (LG), one near Twin Harbors, Wash. (TH), one in Vail, Wash. (VL) and one in the Cascade mountain range in Washington (CA).

The trees were obtained by breeding 71 parents that were a combination of first- and second-generation selections from three first-generation provenances: Cascade, Longview, and Twin Harbors. These select parent were then mated with 4 to 6 "tester" parents from first-generation selections to produce a total of 274 full-sib families. The Genetic Controls (GC) (n=40) were open-pollinated first-generation families that served as a basis of comparison between the first- and second-generation trials. The Field Checks (FC) (n=3) were genetically unimproved seed sources or reference populations used to gauge changes in growth and stem quality through genetic selection.

The full-sib families were arranged as single-tree plots in 6 randomized complete replications. Thus, each site included 6 trees per full-sib family. Genetic Controls were located in 6 sub-blocks within each replication on a site. Each Genetic Control family was represented by 4 single-tree non-contiguous plots within each sub-block. Field Checks were planted in three 99-tree sub-blocks.

Height, diameter, terminal and lateral second flushing, and sinuosity were measured annually from ages 4- to 9-years. Double whorls and ramicorn branching were measured annually from ages 5- to 9-years. Spring bud flush was assessed at 2- to 4-years. Weekly observations were made of the site and when about fifty percent (50%) of the trees had flushed, bud flush was noted and trees were recorded as being early or later spring bud flush trees.

More intensive branch measurements were made on a subset of trees at each test site.

These measurements included branch number and angle, total knot area, and the percentage of fall growth due to second flushing. This sub-set of trees included 30 unrelated parents from 4 of the 6 replications as well as all the trees in 4 of the 6 Genetic Control sub-blocks and 1 of the 3 Field Check sub-blocks.

Final stem quality was assessed in 9-year-old trees in 4 of the 6 replications and retrospectively measured annual leader length, second flushing, ramicorn branching, and sinuosity. Results were averaged across years.

TABLE 1

Descriptions of traits measured and number of observations in the 3 generations of test trees pooled across the four test sites.

| Trait Abbreviation | Number of trees | | | Trait Description |
|---|---|---|---|---|
| | Full-sib | Genetic Control | Field Check | |
| Tree Improvement measures | | | | |
| H8 | 6293 | 898 | 923 | (dm) Tree height at 8-years. |
| D8 | 6293 | 898 | 923 | (mm) Tree diameter at breast height (1.3 m) at 8-years. |

TABLE 1-continued

Descriptions of traits measured and number of observations
in the 3 generations of test trees pooled across the four test sites.

| Trait Abbreviation | Number of trees | | | Trait Description |
|---|---|---|---|---|
| | Full-sib | Genetic Control | Field Check | |
| V8B | 6293 | 898 | 923 | ($dm^3$) Bole volume at 8-years. |
| BudFlush2-4 | 6644 | 947 | 958 | Phenology: 1 = flushed terminal bud. Average based on annual assessments at 2- to 4-years when 50% of trees on a site begin spring budflush (approximately mid-May). |
| Terminal5-9 | 5711 | 791 | 822 | Stem quality: 1 = second flushed terminal bud. Average of annual assessments from 5- to 9-years. |
| Lateral6-9 | 6377 | 913 | 938 | Stem quality: 1 = second flushed lateral bud. Average of annual assessments from 6- to 9-years. |
| Sinu5-9 | 6347 | 902 | 932 | (inches) Stem quality: Sinuosity or the amount of stem deflection from vertical plumb. Average of annual assessments from 5- to 9-years. |
| DWhorl6-9 | 6377 | 913 | 938 | Stem quality: 1 = Double whorl or second whorl of branches from second flushing. Average of annual assessments from 6- to 9-years. |
| Rami6-9 | 6322 | 904 | 934 | Stem quality: 1 = one or more ramicorn branches from second flushing. Average of annual assessments from 6- to 9-years. |
| Tree Improvement intensive branch measures | | | | |
| BranchNumber | 880 | 294 | 621 | Total number of branches >5 mm diameter in whorl and internode immediately above breast height. |
| BranchAngle | 880 | 294 | 621 | Average branch angle in the whorl immediately above breast height. Range was 15° to 37° above horizontal. |
| KnotArea | 880 | 294 | 621 | Total cross-sectional area of all branches calculated from total number of branches multiplied by the average diameter of branches in the whorl and internode immediately above breast height. |
| FallGrowth | 880 | 294 | 621 | Percent of annual height increment due to second-flushing. Measured on internode immediately above breast height. |
| Silviculture measures | | | | |
| Leader5-9 | 4248 | 594 | 929 | (dm) Average of annual height increments from 5- to 9-years. Assessed retrospectively at 9-years. |
| SilvFlush3-9 | 4248 | 593 | 929 | Stem quality: 1 = branch or internode with second-flush. Average from 3- to 9-years assessed retrospectively at 9-years. |
| SilvRami3-8 | 4248 | 593 | 929 | Stem quality: 1 = presence of one or more ramicorn branches. Average from 3- to 8-years assessed retrospectively at 9-years. |
| SilvSinu3-9 | 4248 | 592 | 929 | (inches) Stem quality: Sinuosity or the amount of stem deflection from vertical plumb. Average from 3- to 9-years assessed retrospectively at 9-years. |

Eight-year height was used to eliminate outlier trees from the dataset. Outliers were defined as those with heights that were more than three standard deviations below the average for the site.

Individual tree data was pooled across the four test sites and the data was analyzed with the AS Reml statistical package (available from VSN International Ltd. having an address of 5 The Waterhouse, Waterhouse Street, Hemel Hempstead, Herts, UK HP1 1ES) which fits linear mixed models using restricted maximum likelihood. Factors fitted included the fixed effect of site, the random effects of replicate within test site, the additive effect of each tree as estimated from its phenotype, the numerator relationship matrix, and family effects. Models were fitted both with and without the inclusion of the origin term or parent provenance to determine the origin effect on heritability estimates.

The ASReml model was equivalent to:

$$\text{Trait}_{i,j,k,l,m} = mu + \text{test}_i (+\text{Origin}_m) + (\text{replication:test})_{ij} + \text{family}_k + \text{tree}_l + \text{residual}_{i,j,k,l,m} \qquad \text{II}$$

$\text{Trait}_{ijkl}$ represents the phenotypic value of an individual tree (tree l) for the trait under analysis;

mu is the fitted overall mean for the trait across all four tests;

$test_i$ is the effect of the $i^{th}$ test site (considered to be a fixed effect);

$Origin_m$ is the effect of the $m^{th}$ origin (also fixed);

replication:$test_{ij}$, the effect of the $j^{th}$ block replication within each $i^{th}$ test site;

$family_k$, the non-additive effect specific to the cross that produced full-sib progeny 1. A model was utilised that allowed this effect to be fitted to Set 1 (full-sib) progeny but not Set 2 (half-sib) progeny, as it is assumed that half-sib families do not contain a systematic effect for specific combining ability;

$tree_l$, the additive genetic effect of tree l; and $residual_{ijkl}$, the residual error associated with tree l, assumed to be independent of the test site on which tree l is growing.

The additive genetic relationship matrix describes all known relationships among trees, parents and other ancestors, and its inverse elements augment the equations representing a tree's genetic effect. The additive genetic variance, dominance variance and individual heritability were estimated.

In an individual tree model, the additive genetic variation ($\sigma^2_A$) is given directly by the variance among trees, estimated from all phenotypic information, taking into account known genetic relationships and all other effects in the model.

The variance of family deviations, denoted $\sigma^2_F$, includes all the non-additive genetic variance components, the majority of which is expected to be dominance variance. Dominance genetic variance (denoted as $\sigma^2_D$) was approximated by four times the variance estimated among full-sib families when additive genetic effects are accounted for—

$$\sigma^2_D = 4\sigma^2_F$$

A relatively minor amount of $\sigma^2_F$ will be due to epistatic genetic effects, with this being included in the estimate of $\sigma^2_D$ as calculated here. Note that if there were any non-genetic effects that make members of a full-sib family more alike, this will contribute to the estimate of dominance variance.

Individual heritability ($h^2$) was calculated as the ratio of additive ($\sigma^2_A$) to phenotypic ($\sigma^2_P$) variance among trees—

$$h^2 = \sigma^2_A / \sigma^2_P.$$

The phenotypic variance was calculated as the sum of the additive genetic variance ($\sigma^2_A$), variance due to families ($\sigma^2_F$) and the residual variance ($\sigma^2$)—

$$\sigma^2_P = \sigma^2_A + \sigma^2_F + \sigma^2$$

Variance due to replications was not included in the estimation of phenotypic variance because replication effects were accounted for when estimating breeding values. Standard errors of all components were estimated directly by the ASReml program.

Genetic correlations were estimated in multi-variate ASReml analyses using an individual tree model:

$$(Trait_{m1}Trait_{m2}Trait_{mn})_{ijl} = mu_m + test_{i.m.} + (replication:test)_{ijm.} + tree_{.ijllm.} + residual_{ijlm.} \qquad III$$

where $m_1, m_2 \ldots m_n$ denote the n traits in the multivariate analyses and tree l has a pedigree defined by its known parents and their ancestors. It was not feasible to simultaneously estimate all possible covariances using a maximum likelihood procedure, so the data were analysed in blocks of up to five traits. The additive correlations ($r_A$) between trait1 and trait2 represent the ratio of additive genetic covariance between the traits ($cov_{A1A2}$) over the square root of the additive genetic variances of the same traits ($\sigma^2_{A1}$ and $\sigma^2_{A2}$)—

$$r_A = (cov_{A1A2})/\sqrt{(\sigma^2_{A1}\sigma^2_{A2})}$$

Many traits with repeated measures were averaged over the years of observations for the correlation estimates. A correlation involving one trait with the average of another has the same expectation as the correlation between the first trait and any single component of the second, assuming they are genetically the same trait.

TABLE 2

Genetic correlations comparing year of assessment for spring budflush (e.g., BudFlush4 = assessment at 4-years). Bold numbers on horizontal are individual heritability estimates with standard errors.

| Trait | BudFlush2 | BudFlush3 | BudFlush4 |
|---|---|---|---|
| BudFlush2 | 0.43 ± 0.06 | 0.88 | 0.81 |
| BudFlush3 | | 0.41 ± 0.06 | 0.95 |
| BudFlush4 | | | 0.47 ± 0.06 |

TABLE 3

Efficacy of one- or two-year assessments of lateral flushing and sinuosity as indirect measures of double whorls, ramicorn branching, and sinuosity in a 9-year stem. The table shows individual heritability estimates and genetic correlations between indirect measures and average stem quality traits and volume.

| | Heritability | V8B | DWhorl6-9 | Ramicorn6-9 | Sinu5-9 |
|---|---|---|---|---|---|
| Lateral5 | 0.18 ± 0.03 | 0.14 | 0.92 | 0.91 | −0.02 |
| Lateral6 | 0.21 ± 0.03 | 0.06 | 0.98 | 0.98 | 0.01 |
| Lateral5&7 | 0.29 ± 0.04 | 0.07 | 0.95 | 0.91 | 0.04 |
| SilvFlush3-9 | 0.37 ± 0.05 | 0.22 | 0.93 | 0.93 | 0.03 |
| Sinu5 | 0.21 ± 0.03 | 0.13 | 0.09 | −0.02 | 0.95 |
| Sinu6 | 0.13 ± 0.02 | 0.12 | −0.03 | −0.10 | 0.99 |
| Sinu5&7 | 0.28 ± 0.04 | 0.08 | 0.09 | −0.01 | 0.99 |

While the different embodiment of the invention has been illustrated and described, it will be appreciated that various changes can be made therein without departing from the spirit and scope of the invention.

What is claimed is:

1. A method for selecting a conifer tree for breeding from a group of conifer trees, comprising:
    (a) noting the existence of second flushed lateral buds for a conifer tree in the group of conifer trees by its fifth year of growth;
    (b) noting the amount of sinuosity for the conifer tree by its fifth year of growth;
    (c) measuring the height of the conifer tree by its fifth year of growth; and
    (d) selecting the conifer tree for breeding if it has
        (i) less second flushed lateral buds by its fifth year of growth than a reference population of trees;
        (ii) less sinuosity by its fifth year of growth than the reference population of trees; and
        (iii) greater height by its fifth year of growth than the reference population of trees.

2. The method of claim 1, further comprising noting the time of spring bud flush of the conifer tree in the breeding group of conifer trees at its second year of growth, determining the time when about 50% of the trees in the breeding group of conifer trees spring bud flushed and selecting a plurality of conifer trees from the breeding group of conifer trees, wherein the selected plurality of conifer trees comprises a plurality of trees with a spring bud flush earlier than the time when about 50% of the trees spring bud flushed and a plurality of trees with a spring bud flush later than the time when about 50% of the trees spring bud flushed.

3. The method of claim 1, further comprising:
noting the amount of sinuosity for the tree in the breeding group of conifer trees by its fourth year of growth; and
selecting the conifer tree if it has
no second flushed lateral buds by its fifth year of growth, and
less sinuosity by its fourth year than the reference population of trees.

4. The method of claim 1, further comprising; noting the existence of second flushed lateral buds for the conifer tree by its seventh year of growth;
noting the amount of sinuosity for the conifer tree by its seventh year of growth; and
selecting the conifer tree for breeding if the tree has no second flushed lateral buds by its seventh year and if it has less sinuosity by its seventh year than the reference population of trees.

5. The method of claim 4, further comprising:

measuring the height of the conifer tree by its seventh year of growth;

measuring the volume of the conifer tree by its seventh year of growth; and selecting the conifer tree for breeding if the tree has no second flushed lateral buds by its seventh year, if it has less sinuosity by its seventh year than the reference population of trees, if the height is greater by its seventh year than the reference population of trees, and if it has a greater volume by its seventh year than the reference population of trees.

* * * * *